United States Patent [19]

Shturman

[11] Patent Number: 5,181,911
[45] Date of Patent: Jan. 26, 1993

[54] HELICAL BALLOON PERFUSION ANGIOPLASTY CATHETER

[75] Inventor: Leonid Shturman, Minneapolis, Minn.

[73] Assignee: Shturman Technologies, Inc., Minneapolis, Minn.

[21] Appl. No.: 689,361

[22] Filed: Apr. 22, 1991

[51] Int. Cl.$^5$ .................................. A61M 29/00
[52] U.S. Cl. ........................ 604/96; 606/194
[58] Field of Search ..................... 604/95–103, 604/53, 280; 606/191–194

[56] References Cited

U.S. PATENT DOCUMENTS

| | | | |
|---|---|---|---|
| 1,245,325 | 11/1917 | Dunn. | |
| 3,438,375 | 4/1969 | Ericson. | |
| 4,030,503 | 6/1977 | Clark. | |
| 4,183,102 | 1/1980 | Guiset | 604/101 X |
| 4,515,587 | 5/1985 | Schiff | 604/96 |
| 4,573,966 | 3/1986 | Weikl et al. | 604/53 |
| 4,681,564 | 7/1987 | Landreneau | 604/97 |
| 4,706,671 | 11/1987 | Weinrib | 128/348.1 |
| 4,762,130 | 8/1988 | Fogarty et al. | 128/348.1 |
| 4,934,786 | 6/1990 | Krauter | 604/95 X |

OTHER PUBLICATIONS

Kereiakes, Dean J. and Stack, Richard S., "Perfusion Angioplasty," *Textbook of Interventional Cardiology*, 1990, Section II, Ch. 20, pp. 452–466.

*Primary Examiner*—John D. Yasko
*Attorney, Agent, or Firm*—Gregory P. Kaihoi

[57] ABSTRACT

A perfusion balloon catheter which permits blood flow through the balloon even when the balloon is inflated. The balloon catheter comprises a thin-walled, collapsible and inflatable tube that has a proximal, generally straight portion, and a distal, helically coiled portion that is generally cylindrically shaped and defines an open lumen therethrough. The successive turns of the coil are secured to one another to maintain the balloon's configuration when inflated. The furled balloon catheter can be inserted to the desired location and then inflated. Because the helically coiled portion defines a relatively large open lumen, blood flow through the balloon can continue even as the inflated balloon remains in place, facilitating extended inflation periods.

31 Claims, 17 Drawing Sheets

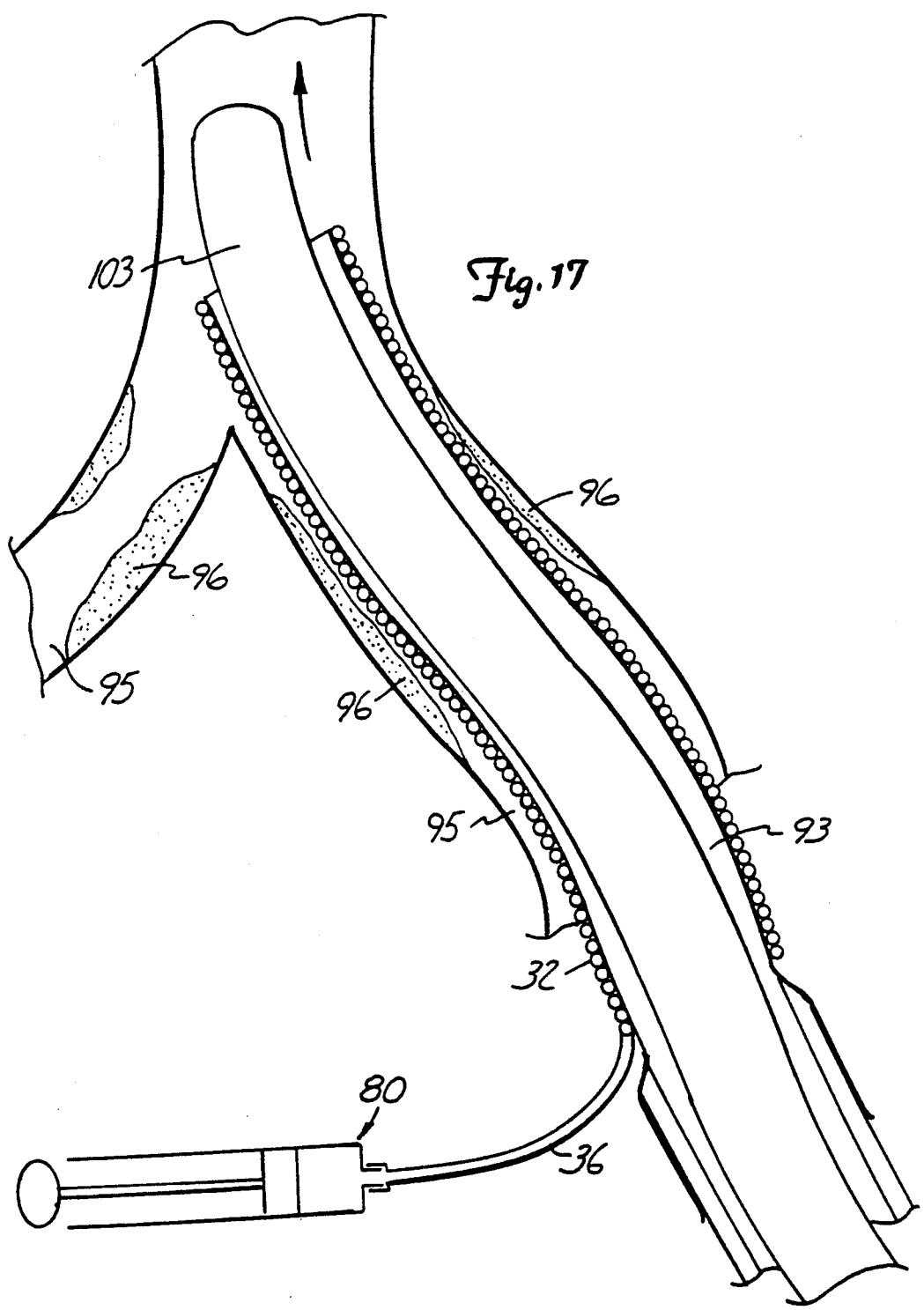

HELICAL BALLOON PERFUSION ANGIOPLASTY CATHETER

FIELD OF THE INVENTION

The invention relates to balloon catheters of the type used in balloon angioplasty and similar medical procedures.

BACKGROUND OF THE INVENTION

Over the last several years great advances have been made in the feasibility and success of balloon angioplasty, both in peripheral arteries and coronary arteries. Percutaneous transluminal coronary angioplasty (PTCA) has now become an established technique for treatment of atherosclerotic obstructions in coronary arteries. For many patients, this procedure eliminates the need to undergo coronary bypass Recent studies have suggested that the effectiveness of balloon angioplasty (including PTCA) increases if the inflation of the balloon can be more gradual and if the duration of balloon inflation can be lengthened. Since conventional balloons entirely occlude the artery when inflated (including any side branches in the artery adjacent the balloon), the duration of balloon inflation often is limited by patient tolerance of chest pain and hemodynamic or electrical instability, as well as eventual tissue necrosis distally of the balloon if the circulation is cut off too long.

A variety of techniques have been proposed to mitigate these limitations, including various drug treatments (e.g., pretreatment with lidocaine, nitroglycerin, etc.), retroperfusion via the coronary sinus, and even the use of general anesthesia. One technique that mitigates many of these limitations is the use of a perfusion balloon catheter, such as that developed by Stack (see, e.g., D. Kereiakes & R. Stack, "Perfusion Angioplasty," *Textbook of Interventional Cardiology* (E. Topol, ed., 1990)). In these types of balloon catheters, the catheter shaft includes side holes both proximally and distally of the balloon. These holes allow blood to enter the catheter lumen proximally of the balloon and then pass through the lumen into the artery distally of the balloon, thus preserving some blood flow even when the balloon is inflated The shaft of such perfusion balloon catheters, however, is necessarily relatively large (in order to permit a significant amount of blood flow therethrough), and the catheter consequently is less flexible, limiting its use and effectiveness. Moreover, side branches of the artery may still be occluded by the balloon if the stenotic segment is near or spans such a branch.

SUMMARY OF THE INVENTION

The invention provides a perfusion balloon catheter that avoids many of the drawbacks of the Stack-type balloon catheter. The balloon catheter of the invention comprises a thin walled collapsable and inflatable tube that has a proximal, generally straight portion, and a distal, helically coiled portion that is generally cylindrically shaped and defines an open lumen therethrough. Means is provided for securing the turns of the coil with respect to one another, such as by providing an outer or inner skin to which the turns adhere.

In use, the furled balloon catheter is inserted to the desired location and then inflated. Because the helically coiled portion defines a relatively large open lumen, blood flow through the balloon can continue even as the inflated balloon remains in place. This allows an extended period of inflation without the side effects attendant with conventional balloons (such as chest pain, etc.). Moreover, the diameter of the central lumen can allow for blood flow equivalent to or greater than the Stack-type balloon, without the size and rigidity problems experienced by those balloons.

Although the turns of the coiled balloon preferably abut one another, in certain embodiments one or more spaces in the helical coil wall can be provided (by spacing successive turns from one another) to facilitate blood flow through arterial side branches that otherwise would be occluded by conventional balloons (including Stack-type balloons). The helical balloon can also be easily configured to have a predetermined bend (or flexibility to bend) for procedures at or very near sharp arterial bends, such as by pre-configuring the balloon with a bend or by providing spaces in the helical coil to give it greater flexibility at certain points.

BRIEF DESCRIPTION OF THE DRAWINGS

FIG. 17 shows a slightly different embodiment of the helical catheter used as an introducer catheter.

BEST MODE FOR CARRYING OUT THE INVENTION

Figure 1:
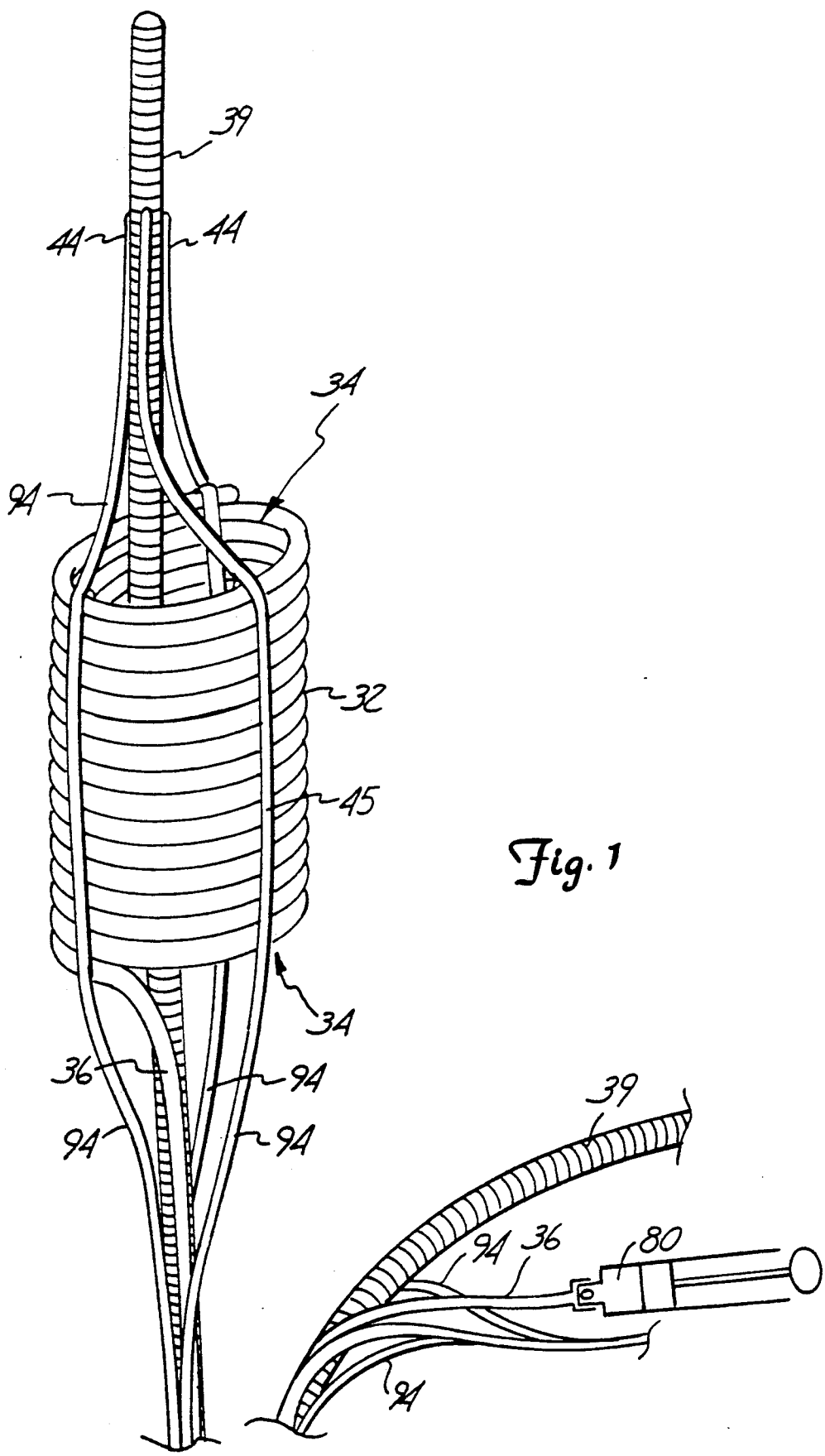
FIG. 1 shows a helical balloon catheter of the invention.

FIG. 1 depicts generally a helical balloon catheter of the invention. The balloon catheter of the invention preferably is comprised of a small thin walled, collapsable tube 32 wound into a helical coil to form a generally cylindrical inflatable balloon portion that has a large open lumen 34 therethrough. The lumen 34 therefore presents a substantially open passageway both distally and proximally, allowing blood to continue flowing through the balloon even when it is inflated.

Successive turns of the helical tube 32 abut one another and are held in position either by adhesive or similar means and/or the intermediate portions 45 of the longitudinal straps 94. In this particular embodiment the straps 94 are attached to a central guide wire 39 at their distal ends 44, and are also attached to the guide wire 39 proximally of the helical portion of the balloon. The proximal portion 36 of the tube 32 itself may also be attached to the guide wire 39, so that the stresses of advancement and withdrawal of the balloon are born by the guide wire 39 and the straps 94, not the tube 32 Such distal and proximal fixation of the straps 94 to the guide wire 39 also longitudinally secures the location of the helical balloon with respect to the guide wire 39. An inflation device 80 is connected to the proximal portion 36 of the tube 32 for inflating and deflating the helical balloon.

Figure 2:
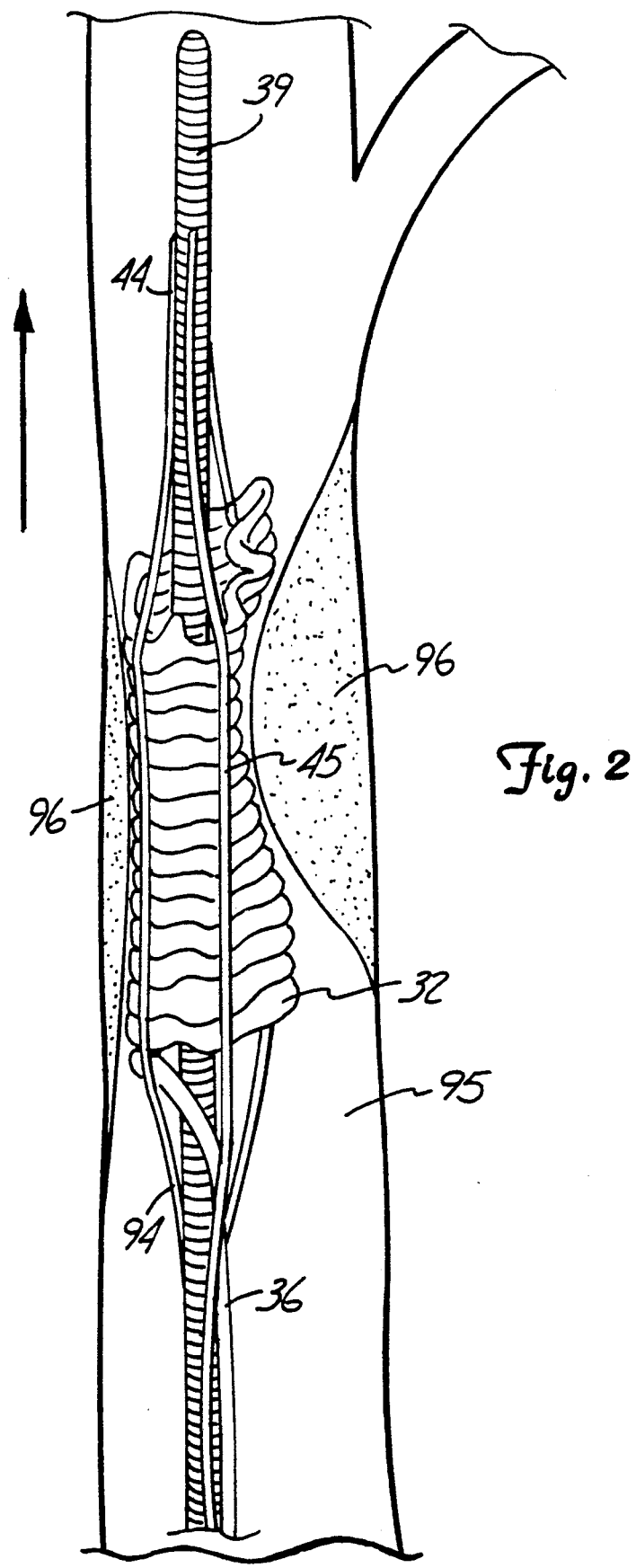
FIG. 2 shows the balloon catheter of FIG. 1 advanced into an artherosclerotic artery and partially inflated.
Figure 3:
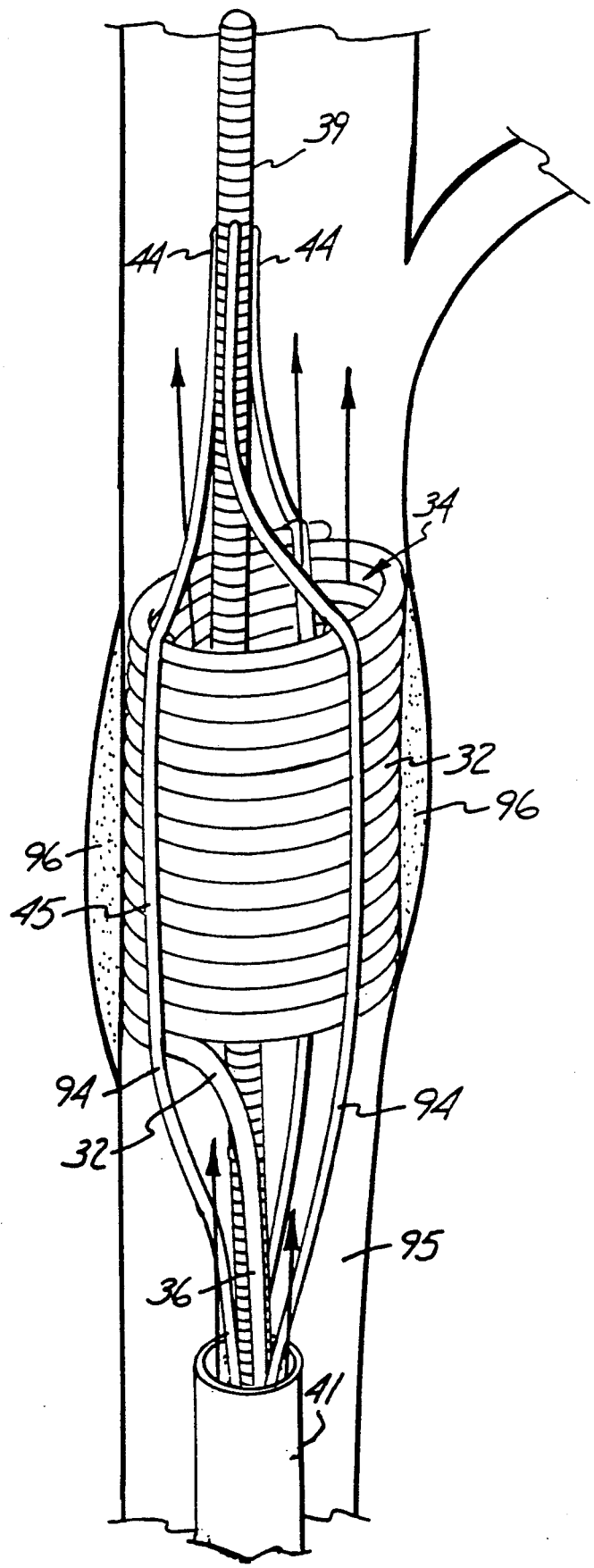
FIG. 3 shows the balloon catheter of FIG. 2 fully inflated with a perfusion or contrast injection catheter advanced over the guide wire.

FIG. 2 depicts the balloon of FIG. 1 in its partially inflated configuration, having been advanced into an artery 95 to a narrowed atherosclerotic portion 96 of the artery 95. In FIG. 3, the balloon has been inflated to expand the the stenotic segment 96 of the artery 95. Because the helical configuration of the balloon catheter provides a large, open lumen 34 when inflated, blood flow through the artery 95 can continue as the angioplasty is being performed, and the balloon can be left inflated for some period of time without restricting blood flow through the artery 95.

Figure 4:
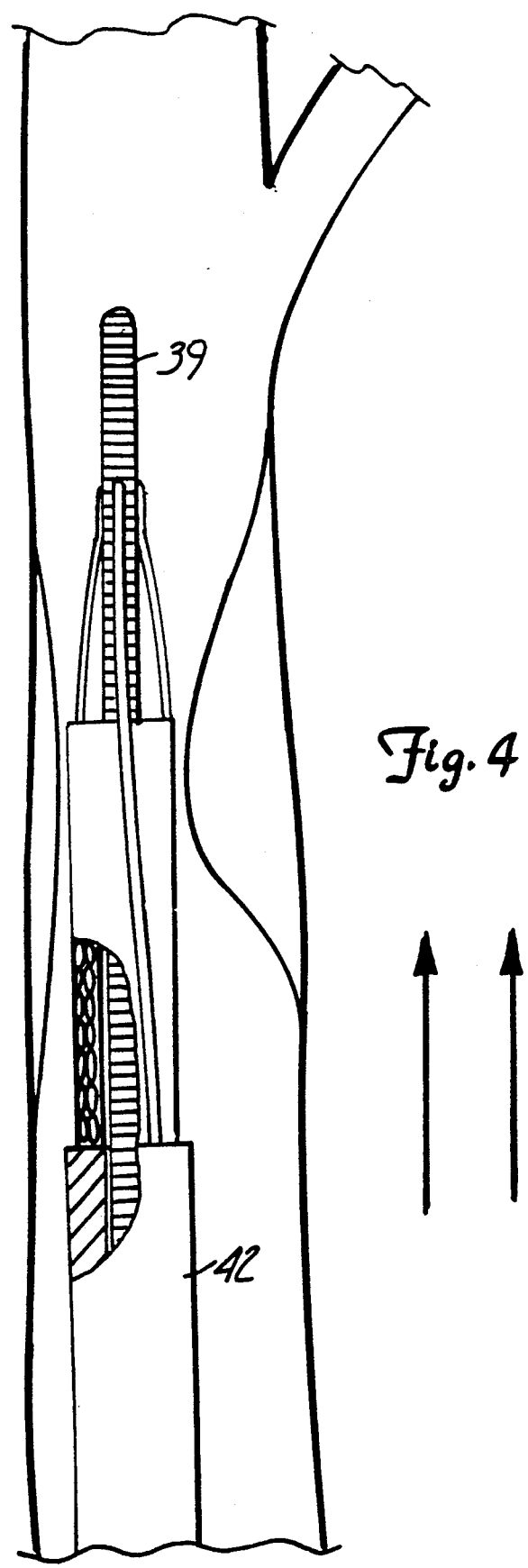
FIG. 4 shows the balloon catheter of the invention in its furled configuration being advanced into an artherosclerotic artery, with a pushing catheter advanced over the guide wire.

If desired, a catheter 41 can be advanced over the guide wire 39 to a position just proximal of the helical portion of the balloon, as shown in FIG. 3. This is useful, e.g., for injecting radiographic contrast to aid in imaging or to perfuse the artery with blood or other solutions from an extra-corporeally located device. Blood autoperfusion through the helical balloon catheter may also be enhanced by blood entering side holes in a proximal portion of the catheter 41, e.g., when the balloon catheter is inserted through the aorta to a coronary artery, the blood enters the catheter 41 side holes in the aorta and then travels through the catheter 41 into the coronary artery and through the helical balloon. The catheter 41 may be made of a much larger diameter than the Stack-type catheters because the balloon is not mounted on it, and in some situations the diameter of the catheter 41 may approach the diameter of the inflated helical balloon placed across the stenotic area, providing significant flow therethrough. When a relatively large diameter catheter 41 is used, it may also serve as a guiding catheter to facilitate balloon catheter/guide wire exchanges FIG. 4 shows that a pushing catheter 42 may also be used to enhance the pushability of the furled helical balloon catheter by transmitting pushing force directly to the furled balloon portion (in addition to the pushing force exerted by the physician on the guide wire 39 itself). The pushing catheter 42 may be advanced over the guide wire 39 to a position abutting the proximal end of the furled balloon portion for assistance in pushing only when actually needed e.g., for the final push in advancing the balloon portion across the stenotic segment of the artery. Moreover, the pushing catheter may be partially withdrawn or entirely removed once the balloon is in place so as not to impede blood flow through the artery.

Figure 5:
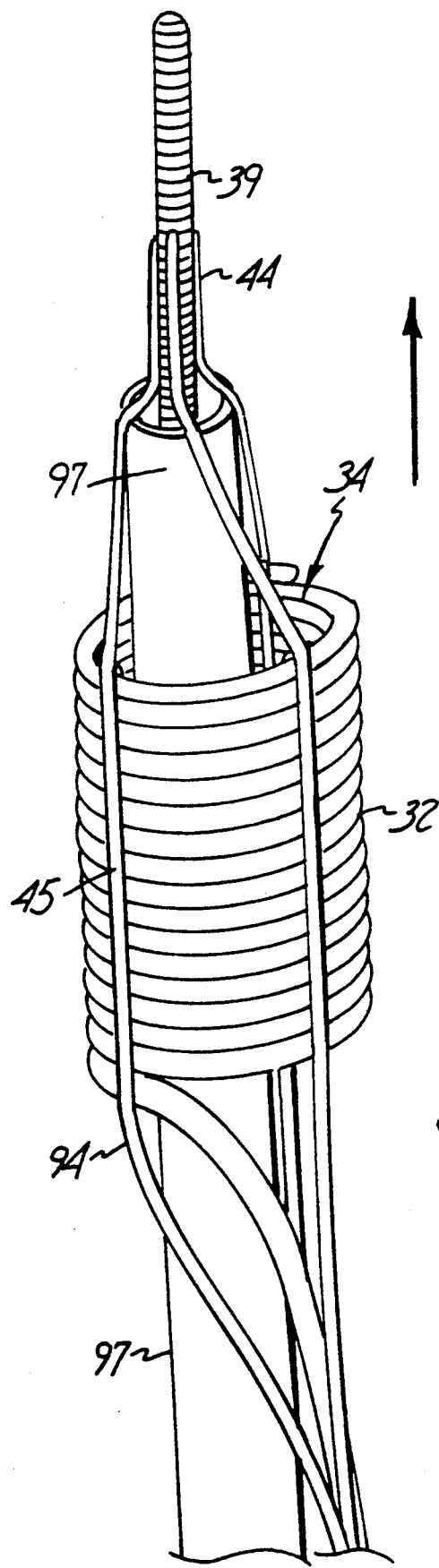
FIG. 5 shows the balloon catheter of FIG. 1 in a slightly different configuration.
Figure 6:
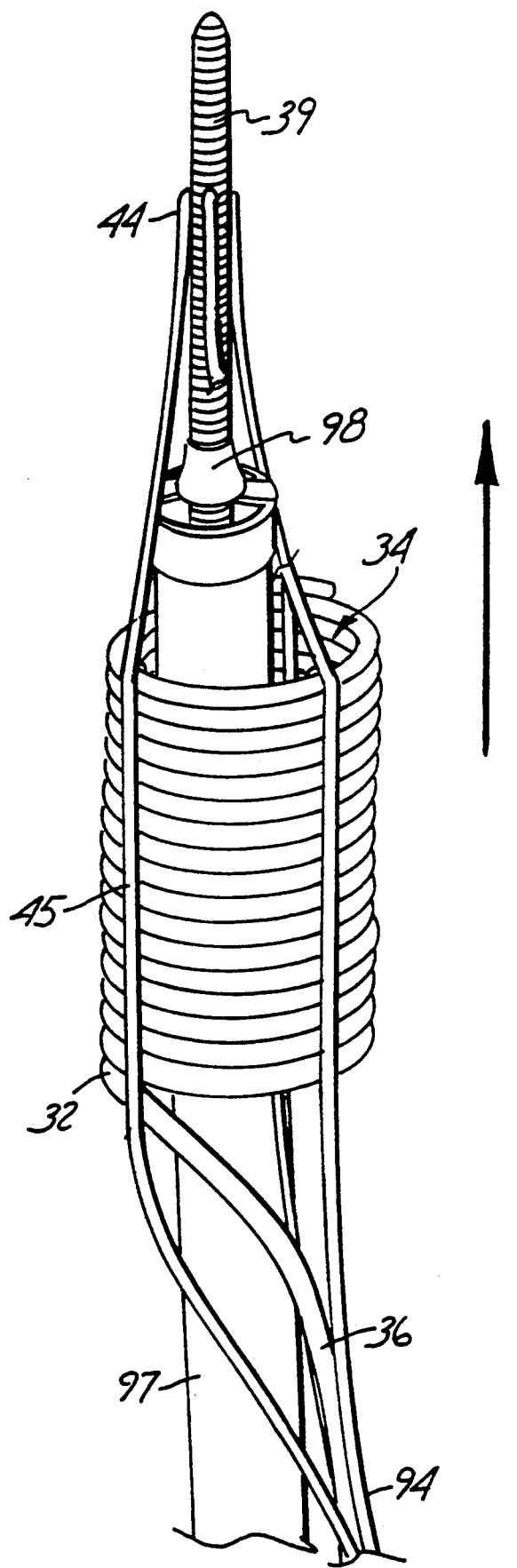
FIG. 6 shows yet another configuration of the balloon catheter.

FIG. 5 shows a slightly modified embodiment of the invention. In this embodiment the straps 94 and tube 32 are not attached to the guide wire 39 proximally of the helical portion so that a more rigid catheter 97 can be advanced over the guide wire 39 beyond the helical portion of the balloon. This is useful, e.g., for increasing the pushability of the guide wire 39. The distal end of this catheter 97 engages the straps 94 near their distal ends 44, pulling the balloon along as the catheter 97 and guide wire 39 are advanced through the artery 95. FIG. 6 shows a modification of this embodiment where the guide wire 39 is provided with a flange 98 that is engagable by the distal tip of the catheter 97 to eliminate stress on the straps 94 as the catheter 97 is used to assist in the advancement of the guide wire 39 and balloon.

Figure 7:
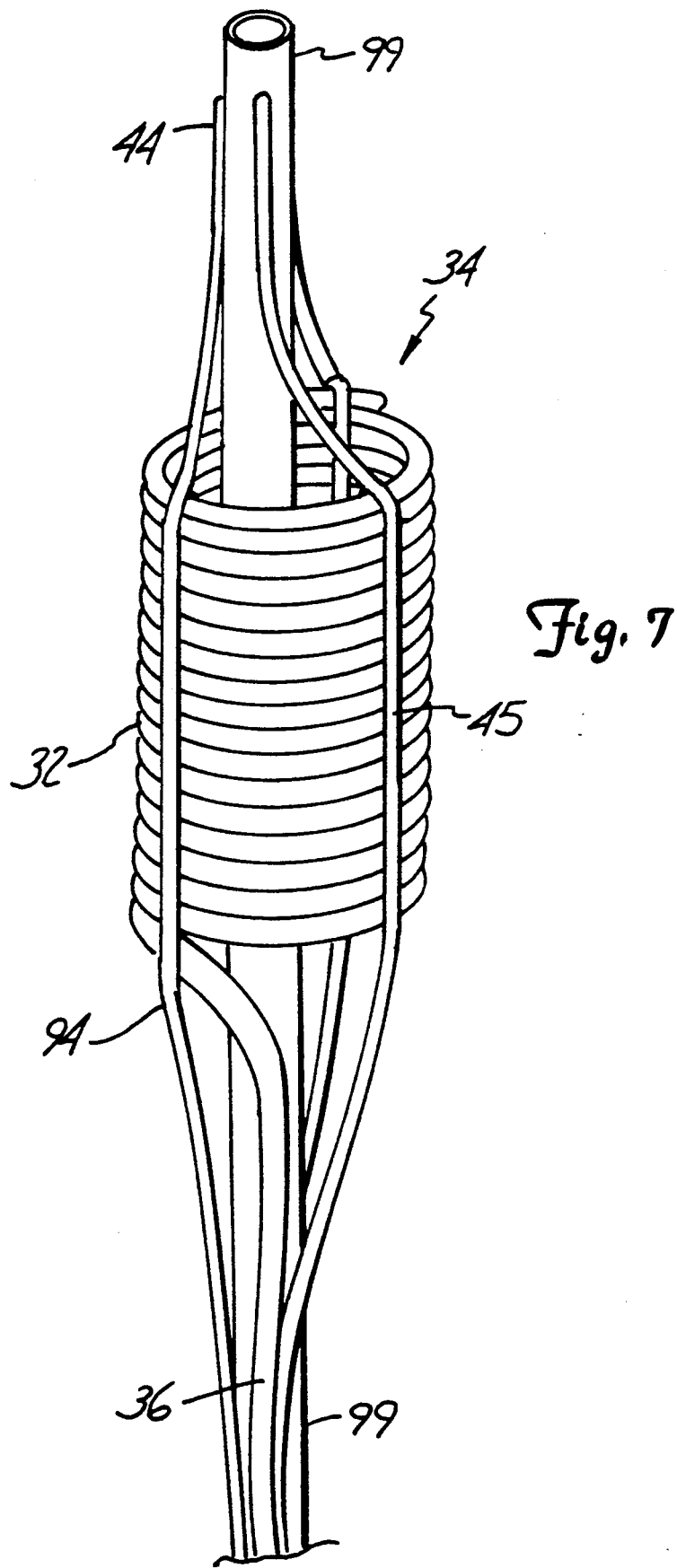
FIG. 7 shows yet a further embodiment of the balloon catheter.

FIG. 7 illustrates an alternate embodiment wherein the straps 94 are attached to a catheter 99 instead of to the guide wire 39. This allows independent advancement and withdrawal of the guide wire 39, but takes up more space in the lumen 34 of the balloon. An additional catheter (not shown) may also be advanced over the catheter 99 until it pushes on the furled balloon, thus further increasing pushability of the system.

Figure 8:
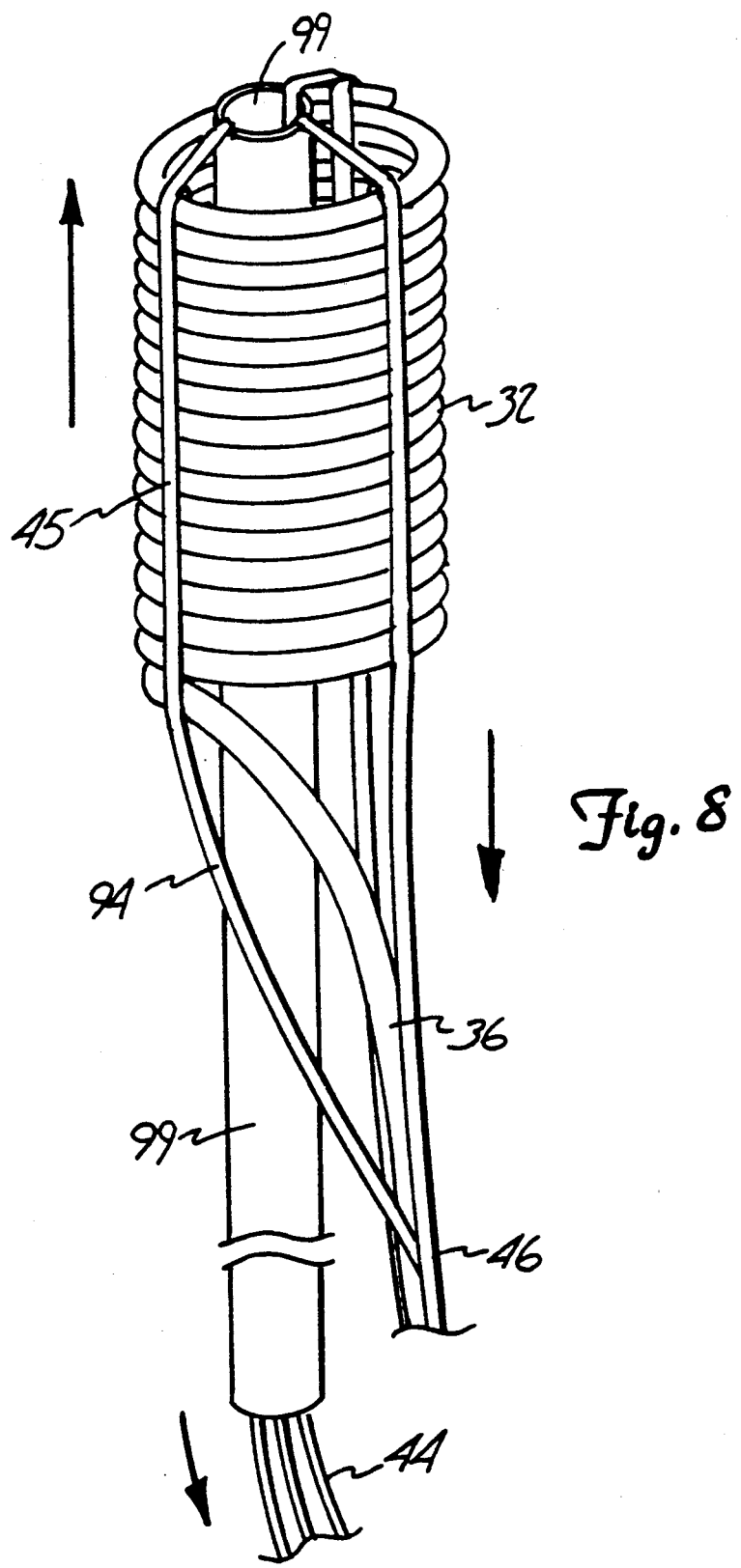
FIG. 8 shows yet a further embodiment of the balloon catheter.

FIG. 8 shows yet another embodiment wherein the distal ends 44 of the straps 94 return proximally through the central lumen of the catheter 99. In this embodiment, the catheter 99 can be advanced or retracted separately with respect to the balloon, but when the physician grasps the distal and proximal ends 44 and 46 of the straps 94 along with the catheter 99 and simultaneously advances or retracts the catheter 99, the balloon will advance/retract as well (since the intermediate portions 45 of the straps are attached to the coiled tube 32).

Figure 9:
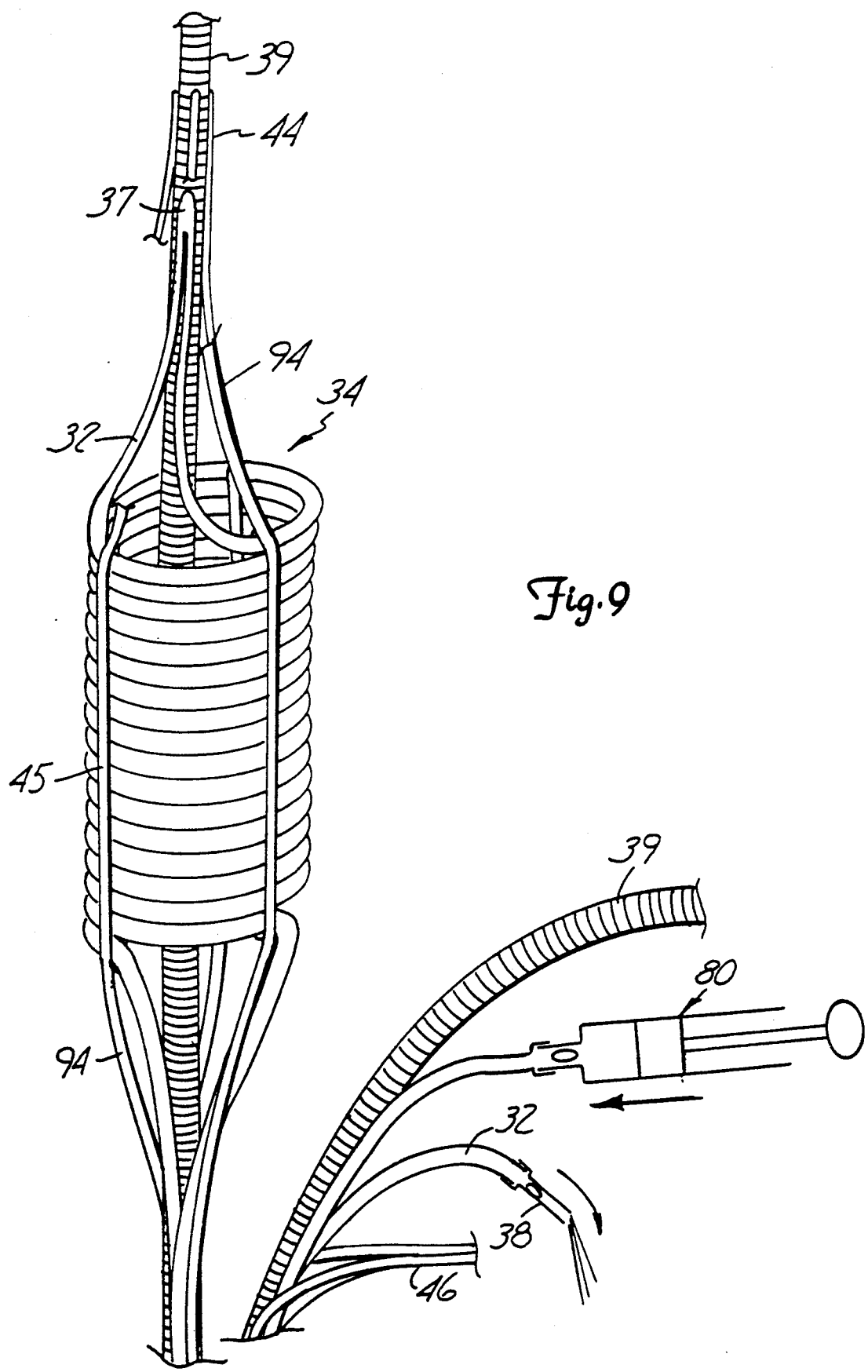
FIG. 9 shows yet another embodiment of the balloon catheter where the tube is folded back upon itself and wound in a double helix fashion.

FIG. 9 shows another configuration for the helical tube 32 in which the helix is formed by a double winding of tube 32, the tube windings being connected to one another at the distal end 37 of the balloon so that, in effect, the balloon consists of a double helical winding of a single tube folded back on itself. In this configuration, the inflation fluid flows into the balloon through one of the windings proximally to distally, and then returns through the other winding distally to proximally. The tube 32 may therefore be entirely flushed of air bubbles, etc., assuring that no air is entrained in the helical tube should the tube burst while in the patient. FIG. 9 shows the inflation/flushing device 80 injecting fluid through the tube, with the fluid exiting through the open stop cock 38 at the opposite end of the tube 32.

Figure 10:
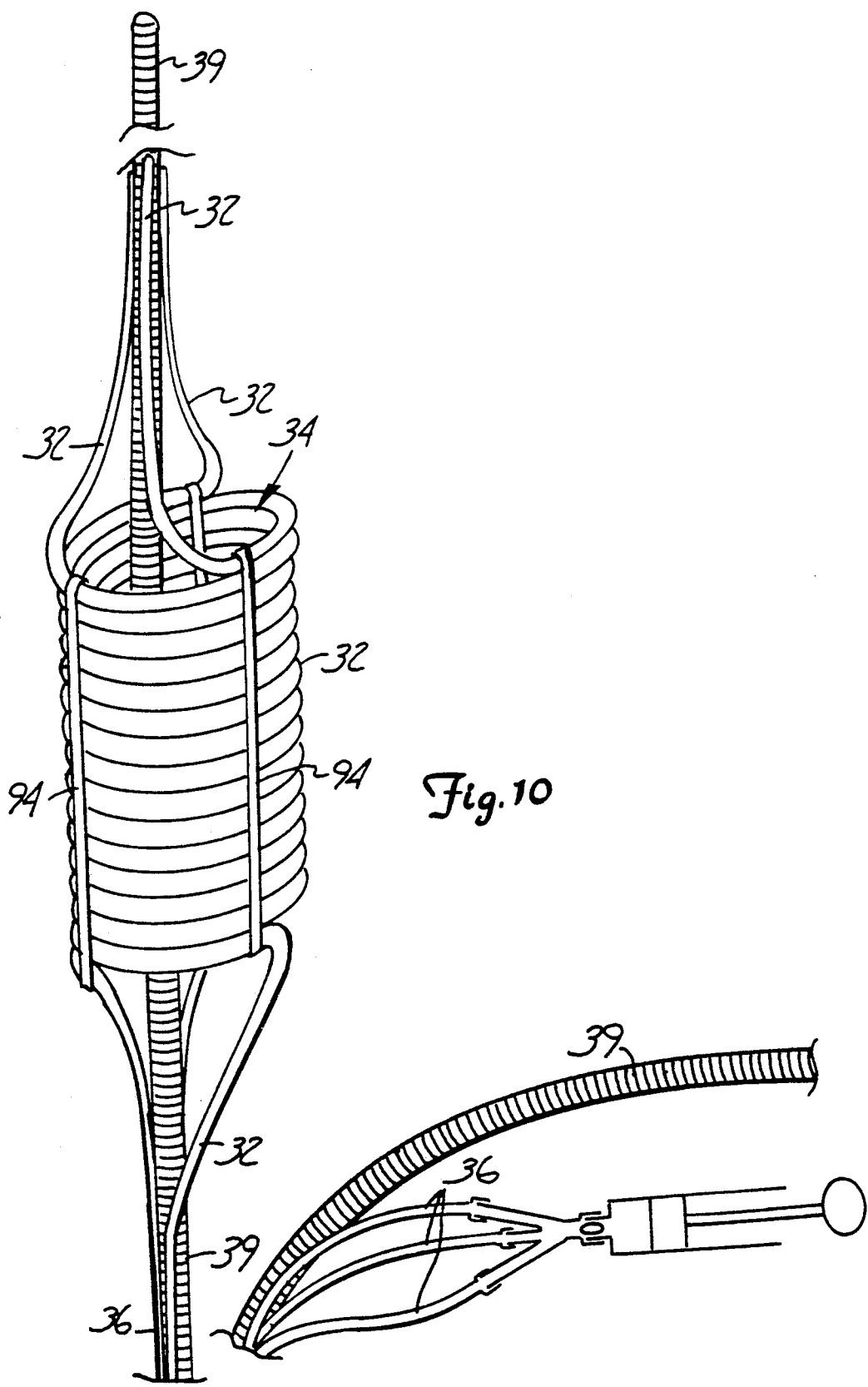
FIG. 10 shows yet another helical balloon catheter having three helically wound tubes.

FIG. 10 illustrates that a triple helical winding may also be utilized if desired to form the balloon. The three tubes 32 forming the balloon are attached to the guide wire 39 both distally and proximally of the helical portion of the balloon, their proximal portions 36 being attached to the inflation device 80. FIG. 10 also shows an alternate arrangement for the straps 94. In this embodiment, the straps 94 are merely fastened around the helical windings, and do not return proximally.

Figure 11:
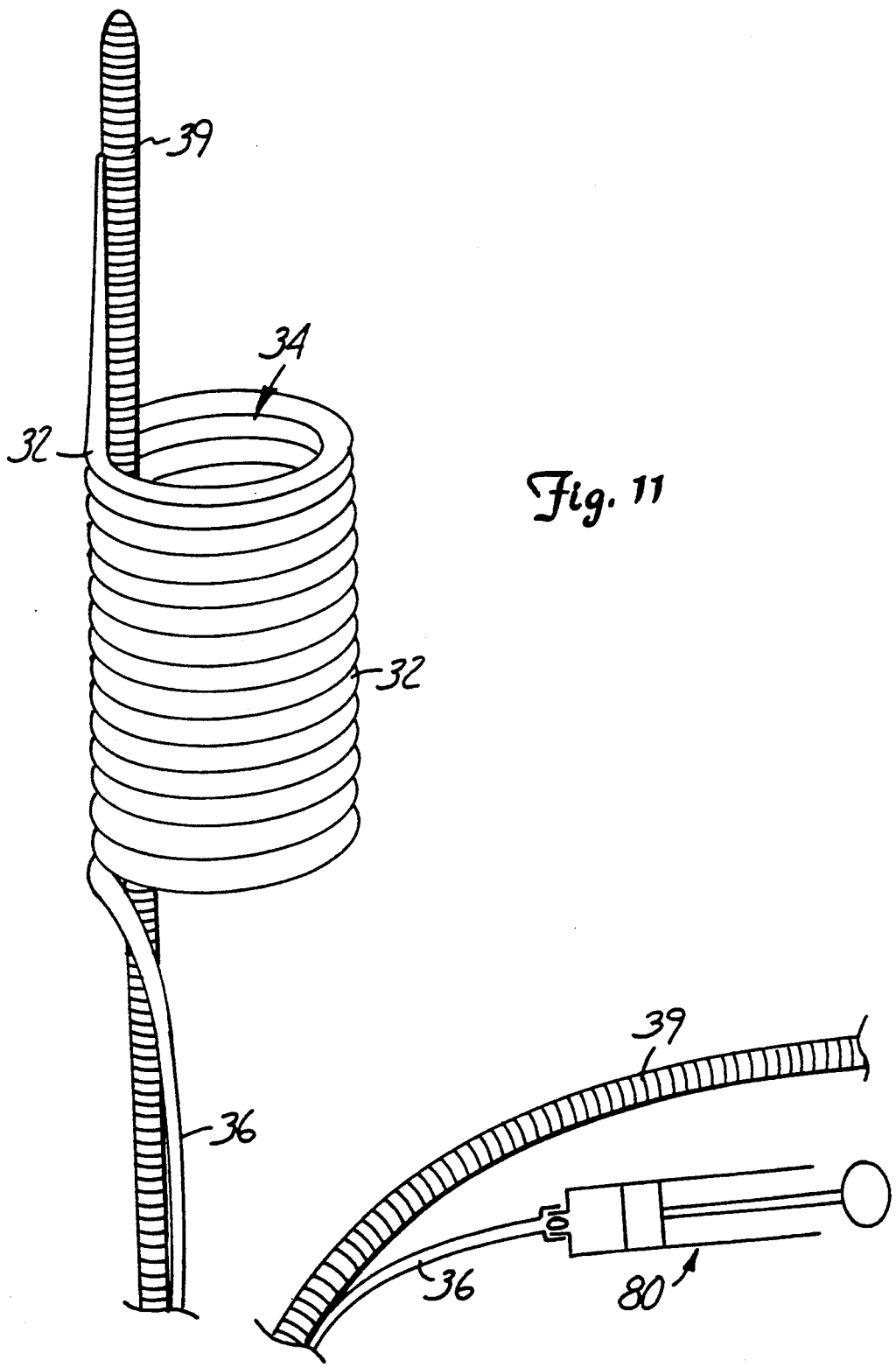
FIG. 11 shows yet another embodiment of the balloon catheter.

FIG. 11 shows yet another configuration in which the helical windings are attached along one side directly to the guide wire 39, eliminating the need for straps 94 entirely. This configuration has the disadvantage that the balloon is not centered about the guide wire 39 when inflated, even though the need for straps is eliminated.

Figure 12:
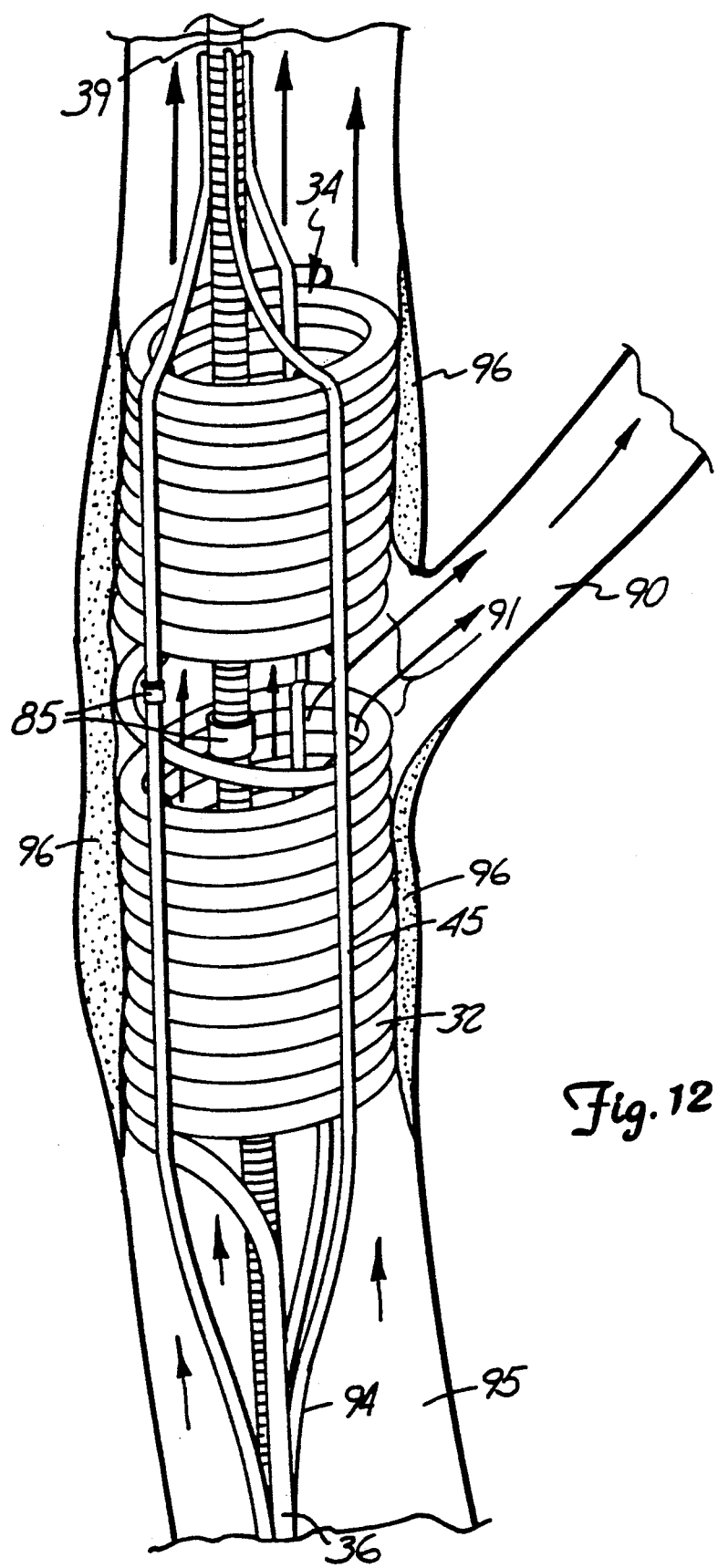
FIG. 12 shows another embodiment having a space between successive turns of the balloon to permit circulation through a side branch artery.

Referring to FIG. 12, if the stenotic segment 96 is located such that the balloon, when inflated, would occlude a side branch 90 of the artery 95, then a modified helical balloon could be utilized that includes a side opening 91, formed by spacing two adjacent turns of the coiled tube 32 slightly from one another. This allows blood to flow out of the lumen 34 into the side branch 90. If desired, radiopaque markers 85 may be placed on the guide wire 39 and/or on the straps 94 to indicate both the longitudinal location of the side opening 91 and the rotational position of the balloon so that the opening 91 in the balloon can be selectively advanced/withdrawn or rotated to the most desirable position.

Figure 13:
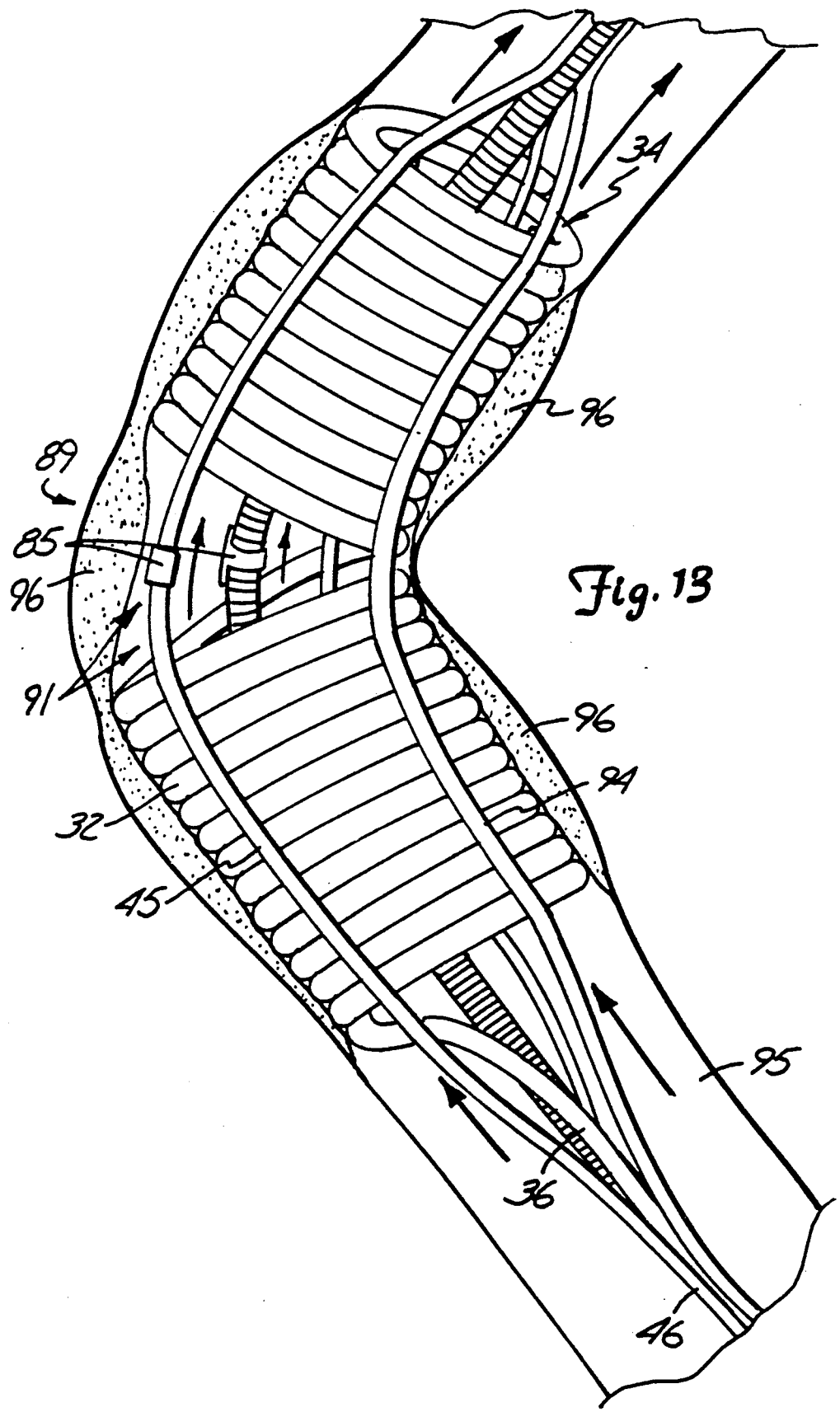
FIG. 13 shows another embodiment having a space between successive turns of the balloon to give the balloon greater flexibility at a midpoint for use at a sharp bend in an artery.

FIG. 13 illustrates another embodiment having a similar opening 91 in the helical balloon. This opening 91 allows the balloon to bend quite dramatically for placement in a bend 89 of the artery 95. The relative lengths of the intermediate portions 45 of the straps 94 can be pre-selected to permit only one side of the balloon to open, thus keeping successive turns of the tube opposite the opening close together, as shown in FIG. 12. Again, radiopaque markers 85 may be used to assist in imaging of the longitudinal and rotational position of the balloon.

Figure 14:
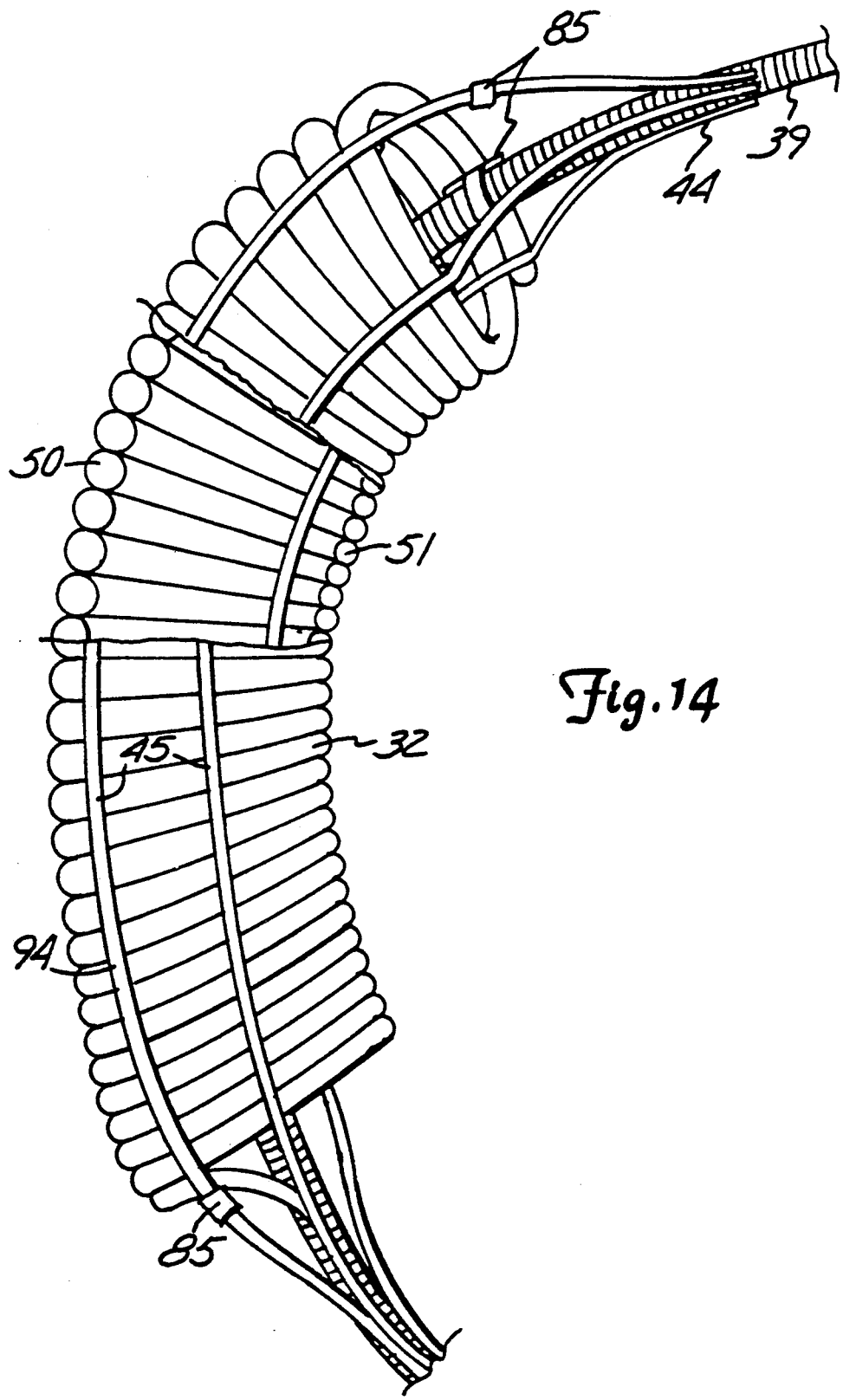
FIG. 14 shows another embodiment having a predetermined curve.
Figure 15:
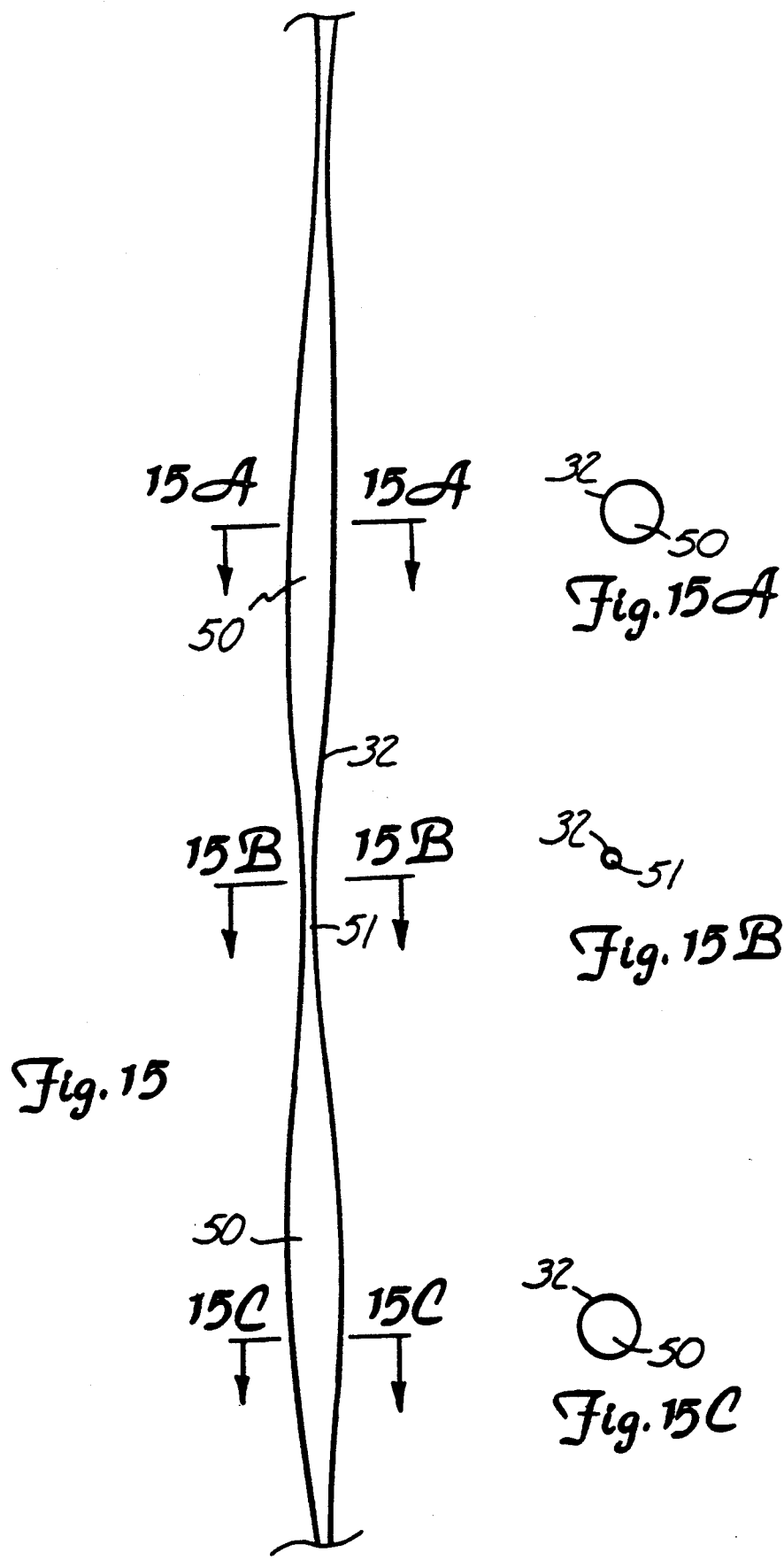
FIG. 15 shows a tube that can be wound into the configuration shown in FIG. 14, with FIGS. 15A–15C showing selective cross-sections through lines 15A—15A, 15B—15B, and 15C—15C, respectively.

FIGS. 14-15 illustrate another technique for manufacturing a balloon with a desired bend. In this embodiment, the tube 32 is manufactured with alternating larger and smaller diameters, as shown in FIG. 15. When wound about a mandrel of the proper corresponding diameter, the larger diameter portions 50 of the tube 32 allign on one side, and the smaller diameter portions 51 allign on the other side, giving the coil a natural bend when inflated.

Figure 16:
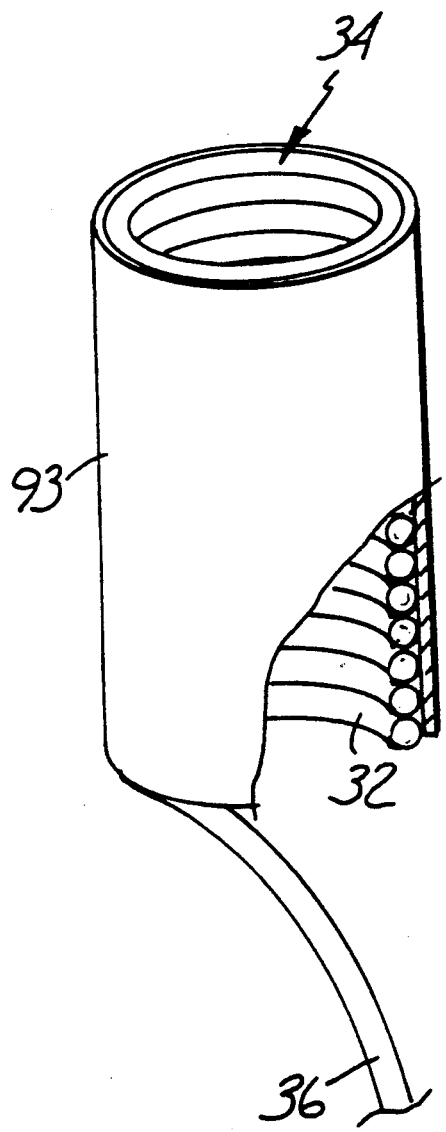
FIG. 16 shows a helical balloon catheter having an outer sheath.

FIG. 16 illustrates one possible technique for manufacturing the helical balloon. The tube 32 may be wound into a coiled tube, and then the turns may be secured by either an inner skin or an outer skin 93 as shown in FIG. 15. Such a skin may be formed by applying a thin layer of adhesive, by securing a thin layer of silicone, or by other conventional means. The thin inner or outer skin 93 may be applied so thinly that it does not significantly change the shape of the undulating surface, or it may be applied somewhat thicker to smooth out the grooves between successive turns of the tube 32, thereby presenting a smooth surface which can be advantageous in certain circumstances. Other similar techniques may also be utilized to produce the desired configuration.

FIG. 17 illustrates an alternate application for use of the helical balloon of the invention in introducing an over-sized device (indicated schematically as 103), for example, through an arthrosclerotic femoral/iliac artery. Here, the helical balloon is advanced while deflated through the femoral/iliac artery 95 to the wider aorta. When the distal end of the balloon has reached the aorta, it may be inflated to present a generally smooth and somewhat straighter pathway for the introduction of devices past arthrosclerotic plaques 96. The use of the inner skin 93 is shown in this embodiment.

While a preferred embodiment of the present invention has been described, it should be understood that various changes, adaptations and modifications may be made therein without departing from the spirit of the invention and the scope of the appended claims.

What is claimed is:

1. A helical balloon catheter comprising an inflatable tube having a proximal, generally straight portion and a distal, helically coiled portion, the helically coiled portion being inflatable from a deflated, furled configuration having a relatively smaller inner and outer diameter to an inflated, unfurled configuration having a relatively larger inner and outer diameter and defining a generally open, central lumen, the balloon further including means for securing turns of the coiled portion with respect to one another.

2. The balloon catheter of claim 1 wherein at least some of the successive turns of the coiled portion abut one another.

3. The balloon catheter of claim 1 wherein the means for securing comprises a flexible skin attached to at least some of the turns of the coil.

4. The balloon catheter of claim 1 further including advancing means for selectively advancing and retracting the coiled portion of the balloon in a bodily passageway.

5. The balloon catheter of claim 4 wherein the advancing means comprises a generally central shaft and attachment means for attaching the coiled portion of the balloon to the shaft.

6. The balloon catheter of claim 5 wherein the shaft comprises a guide wire.

7. The balloon catheter of claim 6 wherein the shaft comprises a catheter.

8. The balloon catheter of claim 5 wherein the balloon is collapsable and capable of being furled closely about the shaft.

9. A helical balloon catheter comprising:
an inflatable tube having a proximal, generally straight portion and a distal, coiled portion defining a generally open, central lumen;
means for securing turns of the coiled portion with respect to one another;
advancing means for selectively advancing and retracting the coiled portion of the balloon in a bodily passageway, the advancing means comprising a generally central shaft and attachment means for attaching the coiled portion of the balloon to the shaft; and
a pushing catheter advancable over the shaft, the pushing catheter having a distal end for pushing against the balloon when it is furled about the shaft.

10. A helical balloon catheter comprising an inflatable tube having a proximal, generally straight portion and a distal, coiled portion defining a generally open, central lumen, means for securing turns of the coiled portion with respect to one another and advancing means for selectively advancing and retracting the coiled portion of the balloon in a bodily passageway, the advancing means comprising a generally central shaft and attachment means for attaching the coiled portion of the balloon to the shaft, the attachment means comprising straps having distal, proximal, and intermediate portions.

11. The balloon catheter of claim 10 wherein the distal portions of the straps are attached to the shaft and the intermediate portions of the straps are attached to the coiled portion of the balloon catheter.

12. The balloon catheter of claim 10 wherein the intermediate portions of the straps are attached to the coiled portion of the balloon, and wherein the shaft comprises a catheter having a distal end and a lumen through which the distal portions of the straps may be threaded so that the catheter can be advanced with its distal end engaging the straps near their intermediate portions to advance the balloon catheter.

13. The balloon catheter of claim 10 wherein the distal portions of the straps are attached to the shaft, and the intermediate portions of the straps are attached to the coiled portion of the balloon, and further comprising a pushability catheter advancable over the shaft and having a distal end so that the pushability catheter can be advanced over the shaft with its distal end engaging the straps near their distal ends to advance the balloon catheter 14. The balloon catheter of claim 13 further comprising a stop carried on the shaft so that the distal end of the pushability catheter engages the stop rather than the straps.

15. The balloon catheter of claim 2 wherein one of the turns of the coiled portion is spaced from a successive turn to form a gap in the coiled portion, permitting perfusion of a branch artery when the balloon is inflated.

16. The balloon catheter of claim 1 including two such inflatable tubes, their coiled portions being coiled in a double helical configuration and being in fluid communication with one another at their distal ends.

17. The balloon catheter of claim 16 wherein the proximal portion of one of the tubes is attachable to an inflation device and the proximal portion of the other tube includes a stopcock that is openable to allow purging of the tube and closable to allow the balloon to be inflated.

18. The balloon catheter of claim 1 wherein the inflatable tube includes first and second ends and is folded upon itself intermediate its ends, the coiled portion thereby comprising a double helical coil adjacent the fold.

19. The balloon catheter of claim 18 wherein the first end of the tube is attachable to an inflation device and the second end of the tube includes a stopcock that is openable to allow purging of the tube and closable to allow the balloon to be inflated 20. The balloon catheter of claim 1 further comprising a shaft disposed within the lumen, the shaft having a surface that is attached to the turns of the coiled portion.

21. A balloon catheter comprising:
an inflatable tube having a proximal, generally straight portion and a distal, coiled, generally cylindrical portion defining an open, central lumen, at least some of the successive turns of the coiled portion abutting one another;
means for securing turns of the coiled portion with respect to one another including a flexible skin attached to at least some of the turns of the coil; and attachment means for attaching the coiled portion of the balloon to a guide wire, comprising straps having distal, proximal, and intermediate portions, the distal portions of the straps being attached to the guide wire and the intermediate portions of the straps being attached to the coiled portion.

22. A balloon catheter comprising a distal, helically coiled, generally cylindrical inflatable sheath portion defining a proximally and distally open lumen, the helically coiled portion being inflatable from a deflated, furled configuration having a relatively smaller inner and outer diameter to an inflated, unfurled configuration having a relatively larger inner and outer diameter, the balloon catheter further including an inflation tube extending proximally from the inflatable sheath portion, and means for advancing and retracting the inflatable sheath portion through a passageway.

23. The balloon catheter of claim 22 wherein the means for advancing and retracting the sheath comprises a shaft attached to the inflatable sheath.

24. The balloon catheter of claim 22 wherein the advancing and retracting means comprises a generally central shaft and attachment means for attaching the inflatable sheath portion of the balloon to the shaft.

25. The balloon catheter of claim 24 wherein the shaft comprises a guide wire.

26. The balloon catheter of claim 24 wherein the shaft comprises a catheter.

27. A balloon catheter comprising a distal, generally cylindrical inflatable sheath portion defining a proximally and distally open lumen, an inflation tube extending proximally from the inflatable sheath portion, and means for advancing and retracting the inflatable sheath portion through a passageway, such means comprising a plurality of straps having proximal, intermediate, and distal portions, the intermediate portions of the straps being attached to the inflatable sheath, and the distal portions of the straps being attached to the shaft.

28. The balloon catheter of claim 27 further comprising a pushing catheter advancable over the shaft, the pushing catheter having a distal end for pushing against the balloon when it is furled about the shaft.

29. The balloon catheter of claim 27 wherein the intermediate portions of the straps are attached to the inflatable sheath portion of the balloon, and wherein the shaft comprises a catheter having a distal end and a lumen through which the distal portions of the straps may be threaded so that the catheter can be advanced with its distal end engaging the straps near their intermediate portions to advance the balloon catheter.

30. The balloon catheter of claim 22 wherein the internal diameter of the open lumen through the inflatable sheath portion is at least about one third of the outer diameter of the inflatable sheath portion.

31. The balloon catheter of claim 22 wherein the internal diameter of the open lumen through the inflatable sheath portion is at least about one half of the outer diameter of the inflatable sheath portion.

* * * * *